United States Patent [19]
Dunn et al.

[11] Patent Number: 5,942,436
[45] Date of Patent: Aug. 24, 1999

[54] CULTURING LIVER CELLS

[75] Inventors: James Dunn, Cambridge; Ronald G. Tompkins, Boston; Martin L. Yarmush, Sharon, all of Mass.

[73] Assignee: The General Hospital Corporation, Boston, Mass.

[21] Appl. No.: 08/797,427

[22] Filed: Feb. 10, 1997

Related U.S. Application Data

[62] Division of application No. 08/331,167, Oct. 28, 1994, Pat. No. 5,602,026, which is a continuation of application No. 07/717,857, Jun. 19, 1991, abandoned, which is a continuation of application No. 07/258,309, Oct. 14, 1988, abandoned.

[51] Int. Cl.$^6$ ...................................................... C12N 5/00
[52] U.S. Cl. .................. 435/325; 435/1.1; 435/289.1; 435/370; 435/375; 435/395; 435/398
[58] Field of Search .................................... 435/325, 370, 435/375, 395, 398, 289.1, 1.1

[56] References Cited

U.S. PATENT DOCUMENTS 4,963,484  10/1990  Naughton et al. .
5,602,026  2/1997  Dunn et al. .

OTHER PUBLICATIONS

Guguen–Guillouzo et al., "Modulation of functional activities in cultured rat hepatocytes", Molecular and Cellular Biochemistry, 53:35–56 (1983).
Reid et al., "Long–Term Cultures of Normal Rat Hepatocytes on Liver Biomatrix", NYAS, 349:70–76 (1980).
Watanabe, "A Fine Structural Study of Liver Culture", Experimenal Cell Reserach, 42:685–699 (1966).
Berry et al., "High–Yield Preparation of Isolated Rat Liver Parenchymal Cells", J. of Cell Biology, 43: 506–520 (1969).
Bissell et al., "Parenchymal Cells From Adult Rat Liver in Nonproliferating Monolayer Culture", J. of Cell Biology, 59: 722–784 (1973).
Phillips et al., "Ultrastructural and Functional Studies of Cultured Hepatocytes", Laboratory Investigation, 31: 533–541 (1974).
Leffert et al., "Growth state–dependent phenotypes of adult hepatocytes in primary monolayer culture", Proc. Natl. Acad. Sci. USA, 75: 1834–1838 (1978).
Michalopoulos et al., "Primary Culture of Praenchymal Liver Cells on Collagen Membranes", Exptl. Cell Res., 94: 70–78 (1975).
Guguen–Guillouzo et al., "Maintenance and Reversibility of Active Albumin Secretion by Adult Rat Hepatocytes Co–Cultured with Another Live Epithelial Cell Type", Research, 143: 47–54 (1983).
Isom et al., "Maintenance of differentiated rat hepatocytes in primary culture", Proc. Natl. Acad. Sci. USA, 82: 3252–3256 (1985).
Clayton et al., "Dependence of Liver–Specific Transcription on Tissue Organization", Mol. and Cell. Biol., 5: 2623–2632 (1985).

Wanson et al., "Adult Rat hepatocytes in Primary Monolayer Culture", J. of Cell Biology, 74: 858–877 (1977).
Hall et al., "Lumen formation by epithelial cell lines in response to collagen overlay: A morphogenetic model in culture", Proc. Natl. Acad. Sci. USA, 79: 4672–4676 (1982).
Agius et al., "Monolayer Culture of Parenchymal Rat Hepatocytes on Collagen–Coated Microcarriers. A Hepatocytes System for Short–and–Long–Term Metabolic Studies", In Vitro Cellular & Development Biology 21: 254–259 (1983).
Bell et al., "Production of a tissue–like structure by contraction of collagen lattices by human fibroblasts of different proliferative potential in vitro", Proc. Natl. Acad. Sci. USA 76: 1274–1278 (1979).
Bell et al., "Living Tissue Formed in vitro and Accepted as Skin–Equivalent Tissue of Full Thickness", Science 211: 1052–1054 (1981).
Bell et al., "The Reconstitution of Living Skin", J. of Investigative Dermatology, 81: 2–10 (1983).
Bell et al., "Reconstruction of a Thyroid Gland Equivalent From Cells and Matrix Materials", J. of Exper. Zoology, 232: 277–285 (1984).
Chambard et al., "Influence of Collagen Gel on the Orientation of Epithelial Cell Polarity", J. of Cell Biology, 91: 157–166 (1981).
Dunn et al., "Hepatocyte Function and extracellular matrix geometry, Long–term culture in a sandwich Configuration", Chem. Abs, V.110, H131723.
Maher, Hepatology 8:1162–1166, 1988.
Montesano et al., "In Vitro Rapid Organization of Endothelial Cells into Capillary–Like Networks is Promoted by Collagen Matrices", J. Cell Biology 97:1648–1652, 1983.
Chen et al., "Three–dimensional culture of rate exocrine pancreatic cells using collagen gels", Br. J. Exp. Path., 66: 551–559 (1985).
Clement et al., "Long–Term Co–Culture of Adult Human Hepatocytes with Rat Liver Epithelial Cells", Hepatology 4: 373–380 (1984).
Demetriou et al., "Replacement of Liver Function in Rats by Transplantation of Microcarrier–Attached Hepatoctyes", Science 233: 1190–1193 (1986).
Emerman et al., "Maintenance and Induction of Morphological DIfferentiation in Dissociated Mammary Epithelium on Floating Collagen Membranes", In Vitro 13: 316–328 (1977).
Hall et al., "Characterization of the Intermediate Filament Proteins of Murine Mammary Gland Epithelial Cells", Exptl. Cell Research, 162: 379–389 (1986).

(List continued on next page.)

*Primary Examiner*—Leon B. Lankford, Jr.
*Attorney, Agent, or Firm*—Fish & Richardson P.C.

[57] ABSTRACT

A method for maintaining hepatocytes in culture includes providing the hepatocytes with a support, the support including extracellular matrix, the support having a configuration that permits each of at least a portion of the hepatpocytes to form at least one apical surface and at least two discrete basal surfaces.

8 Claims, No Drawings

OTHER PUBLICATIONS

Jauregui et al., "Attachment and Long Term Survival of Adult Rat Hepatocytes in Primary Monolayer Cultures", by the Collagenous Substrata, J. of Cell Bio., 98: 146–155 (1984).

Lee et al., "Modulation of Secreted Proteins of mouse Mammary Epithelial Cells by the Collagenous Substrata", J. of Cell Bio., 98: 146–155 (1984).

Lee et al., "Interaction of mouse mammary epithelial cells with collagen substrata", Proc. Natl. Acad. Sci. USA, 82: 1419–1423 (1985).

Michalopoulos et al., "Hormonal Regulation and the Effects of Glucose on Tyrosing Aminotransferase Activity in Adult Rat Hepatocytes Cultured on Floating Collagen Membranes", Cancer Research, 38: 1550–1555 (1978).

Montesano et al., "Collagen Matrix Promotes Reorganization of Panceratic Endocrine Cell Monolayers into Islet –like Organoids", J. of Cell Biology, 97: 935–939 (1983).

Nusgens et al., "Collagen Biosynthesis by Cells in a Tissue Equivalent Matrix In Vitro", Collagen Rel. Res., 4: 351–364 (1984).

Parry et al., "Collagenous Substrata Regulate the Nature and Distribution of Glycosaminoglycans Produced by Differentiated Cultures of Mouse Mammary Epithelial Cells", Exper. Cell Research, 156:487–499 (1985).

Rojkind et al., "Connective Tissue Biomatrix: Its Isolation and Utilization for Long–term Cultures of Normal Rat Hepatocytes", J. of Cell Biology, 87: 255–263 (1980).

Sattler et al., "Ultrastructure of Adult Rat Hepatocytes Cultured on Floating Collagen Membranes", Cancer Research, 38:1539–1549 (1978).

Leffert et al., "Studies on Primary Cultures of Differentiated Fetal Liver Cells", J. of Cell Biology, 52: 559–568 (1972).

CULTURING LIVER CELLS

This is a divisional of application Ser. No. 08/331,167, filed Oct. 28, 1994, now U.S. Pat. No. 5,602,026, which is a file-wrapper-continuation of Ser. No. 07/717,857, filed Jun. 19, 1991, now abandoned, which is a file-wrapper-continuation of Ser. No. 07/258,309, filed Oct. 14, 1988, now abandoned.

BACKGROUND OF THE INVENTION

This invention relates to maintaining vertebrate liver cells in culture.

The vertebrate liver is a complex and indispensable organ that provides many vital functions, including metabolism, excretion, detoxification, storage, and phagocytosis. In humans, acute severe liver failure, such as acute fulminant hepatitis, results from massive hepatocellular necrosis caused by viruses, drugs, or chemicals, and can have a mortality exceeding 80%. Chronic liver failure in humans is most commonly the result of hepatocellular replacement by scar tissue or cirrhosis. Cirrhosis is the sixth leading cause of death in the United States and ranks eight in economic cost among major illnesses; in patients over 40 years old, it is the fifth ranking cause of death.

There exists no satisfactory practical means for liver replacement other than transplantation.

Many approaches to replacing the detoxification function of the liver have been attempted, including nonbiological, biological, and semibiological or hybrid approaches, but few approaches except for whole organ transplantation have had even limited success.

Biological approaches to replacing the detoxification function of the liver have employed transplantation, cross circulation, exchange transfusion, and extracorporeal perfusion.

Human orthotopic liver transplantation for both acute fulminant hepatitis and chronic liver failure now has an actuarial survival of 80% with careful selection of donor and recipient pools. However, owing to donor scarcity and short preservation time of the donor liver, many patients continue to die without transplantation. Heterotopic auxiliary liver transplantation, i.e., emplacement of an additional liver in other than the normal location continues to be explored with limited success in improving survival.

Potential transmission of disease proscribes use of cross circulation between humans, and immunological consequences proscribes its use between a human and a nonhuman animal.

In extracorporeal perfusion, a heterologous liver is used to clear toxins in an extracorporeal circuit, but livers such as porcine or bovine livers degrade after 6 hours or less of such use, and baboon livers degrade within one day. More recent attempts to improve extracorporeal perfusion have included combining it with cross circulation, but with only limited success. These biological approaches have as disadvantages that the surgical techniques are complicated, the immunological consequences are complex, preservation of the livers is difficult, and a high risk exists for transmission of infectious agents such as hepatitis virus or human immunodeficiency virus.

Nonbiological approaches to replacing the detoxification function of the liver have included dialysis, hemoperfusion, and ion exchange.

Dialysis, which is effective in renal failure, has shown no beneficial effect in hepatic coma where membranes are used which remove molecules below 15,000 daltons. Hemoperfusion of blood through charcoal columns removes larger molecules than dialysis, particularly protein-bound toxins, and hemoperfusion may actually reduce morality in acute fulminant hepatitis if therapy is initiated during Stages II or III, which is early in the onset of hepatic encephalopathy; such attempts have been ineffective after onset of irreversible cerebral edema in Stage IV. Passing blood through activated charcoal removes toxins causing hepatic coma, but in an initial clinical trial, overall survival rate was 24% compared to 18% without treatment. Problems with hemoperfusion involving charcoal-induced thrombogenecity and platelet activation have more recently been partly solved by coating charcoal with biocompatible materials, encapsulating the charcoal, perfusing with plasma instead of whole blood, and administrating anti-platelet drugs such as prostacyclin. Both a temporary recovery of consciousness and improved survival have been reported with coated charcoal hemoperfusion in acetaminophen-induced fulminant liver failure in humans.

Although these studies have shown limited positive effects, non-biological methods are for the most part inadequate because of their monofocal approach. Major liver functions, such as, for example, metabolism, synthesis, and storage are ignored in these nonbiological systems. It is also likely that some toxins are left in the circulation while some salutory regeneration factors are removed.

Combinations of biological and nonbiological approaches into semibiological or hybrid approaches to replacing the detoxification function of the liver have utilized a combination of enzymes or cells or tissues with mechanical devices, such as immobilized enzymes, dialysis membranes with single cell hepatocyte suspensions or liver slices, and hepatocytes immobilized in alginate, or fetal hepatocyte cells growing on hollow fiber capillaries. Enzyme immobilization using enzymes important in liver function, and using charcoal, red cell ghosts, hollow fibers, and artificial cells as solid-phase supports, is limited in that only one substrate is altered with each such treatment, and it is too simplistic an approach for liver failure in view of the fact that hepatic coma appears to result from more than one different toxin.

An approach combining dialysis with liver pieces or single cell suspensions enclosed within a reactor through which blood is perfused have been effective in lowering toxin concentrations. In such systems, however, oxygen transfer and movement of protein-bound toxins is limited by diffusion and the friable consistency of the liver does not allow the preparation of slices sufficiently thin to overcome these diffusional limitations.

One approach to overcoming the diffusional limitations inherent systems described above involves transplanting a liver cell suspension into a site such as the peritoneal cavity, the spleen, and the lung. Syngeneic, allogeneic, and xenogeneic hepatocyte transplantations in animals have resulted in improved survival rates, but rejection of allogeneic or xenogeneic transplants is expected. In combination with immunosuppression, hepatocytes attached to microcarriers have been demonstrated to replace glucuronyl transferase activity in Gunn rats and albumin production in Nagase rats. Ideally, protection of the transplanted hepatocytes from graft rejection is desired. To this end, entrapment of hepatocytes in collagen, alginate, agarose, and urethane prepolymer has been tried using configurations such as spherical gel beads and cylindrical hollow fibers. However, these protective barriers can impose significant mass transfer resistances, and thus can limit the viability and/or function of the protected cells.

Hepatocytes are difficult to maintain in a viable condition, and hepatocytes maintained in culture lose their liver phenotype over short time periods. Hepatocytes are anchorage-dependent, highly differentiated cells that are difficult to maintain in vitro, Guguen-Guillouzo (1983), Molec. cell Biochem., Vol. 53/54, pp. 35–56; Reid, et al., (1984), Hepatology, 4(3), pp. 548–559. Early attempts to culture liver cells from organ explants invariably led to overgrowth of fibroblasts and undefined epithelial cell lines, Watanabe (1966), Exp. Cell Res., Vol. 42, pp. 685–699. Short-term cultures of hepatocytes became possible with the introduction of enzymatic dissociation of the liver, Berry et al. (1969), J. Cell Biol., Vol. 43, pp. 507–520, resulting in large number of cells that were mostly hepatocytes. Conventional culture configurations include cell suspensions in stirred flasks and cell monolayers on plastic dishes, Bissell et al. (1973), J. Cel Biol., Vol. 59, pp. 722–734, Phillips et al. (1974), Lab Inv., Vol. 31, pp. 533–542. Hepatocytes in suspension cultures cluster into large clumps of cells within one day of incubation, with rapid loss of function. Hepatocytes in monolayer cultures dedifferentiate and lose adult liver phenotype within a week of incubation. Generally speaking, these cultures tend to fetalize with age of culture, Leffert et al. (1978), Proc Natl. Acad. Sci., Vol. 75, pp. 1834–1838, expressing fetal pyruvate kinase isozymes or α-fetoprotein. These hepatocytes gradually die and eventually detach; concomitantly other cell types grow to overtake the culture.

More recently, efforts were made to culture hepatocytes in arginine-free media, Leffert et al. (1972), J. Cell Biol, Vol. 52, p. 559, on floating collagen membrane, Michalopoulos et al. (1975), Exp. Cell Res., Vol. 94, p. 70, on liver biomatrix, Reid et al. (1980), Ann. NY Acad. Sci., p. 70, along with other liver cells, Guguen-Guillouzo et al. (1983), Exp. Cell Res., Vol. 143, p. 47, and in the presence of dimethyl sulfoxide, Isom et al. (1984), PNAS, Vol. 82, p. 3252. In each of these approaches, liver-pecific functions were shown to be maintained for periods ranging from 2 to 7 weeks. However, Clayton (1985), Molec. Cell Bio., Vol. 5, p. 2623, showed that none of these cultures exhibited normal liver specific transcriptional rate; the level of liver-specific MRNA was, at best, kept at a constant level by stabilizing the original mRNA.

Hepatoma cell lines and some liver-derived cell lines grow well in vitro, but it has been found that these cell lines often lack many liver-specific functions, Clayton et al., (1985), Molec. Cell Biol., Vol. 5, p. 2633, and the tumorigenic nature of these cells limits its application in clinical situations.

Several methodological approaches to improving both morphology and function of cultured hepatocytes have been reported including addition of extracellular matrix products, addition of other cell types, and use of different media formulations. Leffert (1972), J. Cell Biol., Vol. 52, pp. 559–568; Michalopoulos et al., (1975), Exp. Cell Res., Vol. 94, pp. 70–78; Reid L. M., et al. (1980), Ann. NY Acad. Sci., pp. 70–76; Guguen-Guillouzo et al. (1983), Exp. Cell Res., Vol. 143, pp. 47–54; Isom et al., (1985), Proc. Natl. Acad. Sci., Vol. 82, pp. 3252–3256. Except for the use of matrix components as a substrate for hepatocyte culture, these methods face serious limitations when clinical implementation is considered. For example, it would be difficult to maintain an arginine-free environment once the hepatocytes are used as an artificial liver support; DMSO toxicity limits its use in patients with liver failure; and introduction of undefined epithelial cell lines into patients is clinically unacceptable.

It has been shown that when a suspension of liver cells is seeded on a culture dish, cells tend to reorganize such that they reconstitute many histological landmarks such as the bile canaliculus, Wanson et al. (1977), J. Cell Biol., Vol. 77, pp. 858–877. However, under known culture conditions the cells maintain this "in vivo-like" configuration only for a short time, and thereafter lose their structural and metabolic character as liver cells.

It is known that extracellular matrix and cell-cell interaction can influence the behavior and differentiation of cells. Polarization of cultured cells in response to addition of extracellular matrix has been demonstrated in several instances. For example, after collagen is overlayed on a monolayer of mammary epithelial cells cultured on collagen gel, cells reorganize to form structures with their lumens directed away from the collagen, Hall, et al. (1982), Proc. Natl. Acad. Sci., Vol. 79, pp. 4672–4676. Such tube-like structures resemble the mammary ducts that are present in vivo. This, of course, is the natural configuration of mammary epithelial cells, which line ducts in a monolayer fashion. The formation of a flat monolayer on a dish is an artifact of the physical constraints imposed by the culture environment.

Addition of extracellular matrix products, such as collagen, to cultures of hepatocytes can somewhat improve the maintenance of differentiated functions.

SUMMARY OF THE INVENTION

We have discovered that, when hepatocytes are provide with a support in the form of an extracellular matrix in a configuration that permits the hepatocytes to form at least one apical surface and at least two basal surfaces, the hepatocytes can be maintained in culture for extended periods without loss of functions characteristic of adult hepatocytes in vivo.

In general, in one aspect, the invention features a method for maintaining hepatocytes in culture, including providing the hepatocytes with a support, the support including extracellular matrix, the support having a configuration that permits each of at least a portion of the hepatpocytes to form at least one apical surface and at least two discrete basal surfaces.

In preferred embodiments, the extracellular matrix is Type I collagen; the configuration is a sandwich configuration, or a gel suspension configuration.

Histologic examination reveals the liver as a highly organized epithelial tissue that possesses an unusual polarity. Unlike the classical epithelium as exemplified for example by intestinal mucosal cells, each hepatocyte generally has at least one belt of apical surface and at least two basal surfaces. Hepatocytes secrete albumin across the basal surface and excrete bile salts across the apical surface.

Hepatocytes are epithelial cells that have distinct apical (bile canalicular) and basal (sinusoidal) surfaces that serve different functions in vivo. For example, bile acids are excreted into the bile duct by traversing the apical surface, whereas albumin is secreted into the circulation by traversing the basal surface. Normal function of hepatocytes would appear to be related to this polarization, as the normal function of epithelial cells generally is related to cell polarization. However, hepatocytes in vivo typically have two basal surfaces, rather than only one, as is characteristic of a classical epithelium, and in vivo both of these basal surfaces are in contact with extracellular matrix; and each hepatocyte in vivo typically has a "belt" of apical surface which divides the two basolateral surfaces. As distinguished from most epithelial structures, which normally rest on one sheet of basement membrane, both of the basal (or basolateral) sides of each hepatocyte are in contact with extracellular matrix, and adjacent hepatocytes are in vivo typically closely associated with each other at their apical surfaces through junctional complexes and adhesion molecules.

DESCRIPTION OF THE PREFERRED EMBODIMENTS

The example which follows illustrates a preferred embodiment of the method of the invention in which the extracellular matrix is provided in two layers, and the hepatocytes are positioned between the layers, to form a sandwich configuration. It will be appreciated that such a sandwich can be constructed by techniques differing in particulars from those described in this example, and that the sandwich can have different shapes and yet still provide a configuration within the invention, that is, a configuration that permits each of at least a portion of the hepatocytes to have contact with the extracellular matrix support on at least two basal surfaces.

The technique described in this example for providing a support in a sandwich configuration generally includes providing a suspension of hepatocytes, preparing a solution of an extracellular matric component, forming a first gel layer of the extracellular matrix, seeding the surface of the first gel layer with a suspension of the hepatocytes and permitting the hepatocytes to attach to the surface, and forming a second gel layer over the surface of the first layer, covering the hepatocytes. A detailed protocol follows.

EXAMPLE

Sandwich Configuration

Isolation of Hepatocytes

Rat hepatocytes were isolated from two-month old female Lewis rats, weighing 180 to 200 grams, using a modification of the procedure described in Seglen (1976), Methods in Biology, Vol. 13, p. 29. Briefly, after ether anesthesia, the portal vein is cannulated and the hilus is tied off. The liver, weighing roughly 8 grams, is perfused with 500 ml of calcium-free Krebs Ringer bicarbonate buffer, containing 5.5 mM glucose and 20 mM HEPES buffered at pH 7.4, at 50 ml/min. The perfusate is maintained at 37° C. by a heat exchanger and is equilibrated with 95% $O_2$/5% $CO_2$. Near the end of the 500 ml of perfusate, the blanched liver is transferred to a recirculating circuit to allow enzymatic digestion with 100 ml of 0.05 g/dl collagenase solution with 5 mM $CaCl_2$ for 10 minutes. The fibrous capsule of the softened liver is teased apart to allow liberation of freed cells. The cell suspension is filtered through two nylon meshes (Small Parts), with grid sizes 250 $\mu$M and 62 $\mu$M. The filtrate is centrifuged at 50 g for 5 minutes, and the pellet is resuspended in 50 ml of Dulbecco's Modified Eagle Medium (DMEM, high glucose, with L-glutamine, without pyruvate, Hazleton).

Cells were further purified using a modification of the procedure described in Kreamer et al. (1986), In Vitro cell Dev Bio, Vol. 22, p 201. Briefly, 12.5 ml of cell suspension is added to 10.8 ml Paercoll (Pharmacia) and 1.2 ml 10× DMEM. This mixture is centrifuged at 500 g for 5 minutes, and the resulting pellet is washed twice with DMEM. Viability is assessed with 0.04 g/dl Trypan Blue at one minute. Routinely, 200 to 300 million cells are isolated from one rat liver, with viability ranging from 90% to 98%. As judged by their size and morphology, the non-hepatocyte cellular elements represent less than 1% of the cells present.

Preparation of the Extracellular Matrix

Collagen derived from rat tail is used as an extracellular matrix material in this example. Rat tail tendon is prepared by a modification of a procedure described by Elsdale et al. (1972), J. Cell Bio., Vol 54, p. 626. Briefly, four tendons are dissected from each rat tail and are left stirring in 200 ml of 3% acetic acid overnight at 4° C. The solution is filtered through four layers of cheesecloth and is centrifuged as 12,000 g for 2 hours. The supernatant is precipitated with one-fifth volume of 30 g/dl NaCl, and the pellet is collected by centrifugation at 4,000 g for 30 minutes. After two rinses with 5% g/dl NaCl and 0.6% acetic acid, the pellet is redissolved in 0.6% acetic acid. The solution is dialyzed against 1 mM HCl and is then sterilized by the additional of chloroform. A five ml aliquot is lyophilized to determine the concentration. Generally, 200 mg can be isolated from one rat tail. Collagen gel prepared by rapidly mixing the collagen solution with 10× DMEM and incubating at 37° C.

Preparation of the Double Gel Support

One ml of collagen gel prepared as described above is evenly distributed over a 60 mm tissue culture dish (Falcon) at least one hour before use. Unless otherwise specified, two million viable cells are seeded in 4 ml of "complete" medium, containing 10% (vol:vol) fetal bovine serum (Hazleton), 0.2 U/ml insulin (USP, Squibb), 0.007 $\mu$g/ml glucagon (USP, Lilly), 0.02 $\mu$g/ml Epidermal Growth Factor (EGF, Collaborative Research), 7.5 $\mu$g/ml hydrocortisone sodium succinate (Solu-Cortef, Upjohn), and 2,000 U/ml penicillin (USP, Hazleton), and 2,000 $\mu$g/ml streptomycin (USP, Hazleton). Cultures are incubated in 10% $CO_2$ and air.

After at least 24 hours in culture, a second layer of collagen gel (an overlay) is spread over the cells in order to create a "double-gel" support. Thirty minutes is allowed for gelation at 37° C. of the second layer of collagen and to allow attachment of this second layer of collagen to the culture system before the "complete" medium is replaced. Culture medium ("complete" media) is changed daily for optimal results.

Assay for Maintenance of Hepatocyte Function

As a first order indication that the hepatocytes maintained in culture in the sandwich configuration of this example are retaining metabolic functions phenotypically characteristic of hepatocytes in vivo, collected media were analyzed for rat serum albumin concentration by ELISA.

For DNA analysis, cells were harvested from cultures in collagen gel by collagenase digestion, and DNA concentration was analyzed with Hoechst dye 33258.

Morphologically, when the seeding density was 100,000 viable cells per $cm^2$ in 4 ml of complete medium in a 60 mm dish, hepatocytes attached within one hour and started to spread by three hours. Some non-viable cells attached, but they remained spherical and took up trypan blue. Viable cells clustered into cords covering roughly half of the surface area and exhibited polygonal morphology typical of hepatocytes. Overlaying these cells with collagen gel did not appear to disturb the cells. After overlaying with the second layer, the hepatocytes were "immobolized" and spread slowly until ultimately a confluent monolayer of cells was achieved at two weeks. These hepatocytes maintained their polygonal morphology throughout the seven weeks. Hepatocytes cultured on collagen without the overlay, on the other hand, spread much more rapidly, achieving a confluent monolayer by the third day. These hepatocytes were thinner and larger as compared to ones sandwiched between collagen gels. Cells appeared to die and detached continually in this system. By the fifth day, significant holes appeared in the monolayer, resulting in patches of hepatocytes. Cells within these patches often appeared to fuse, forming multinucleated giant cells. Non-hepatocytes were present in negligible numbers in the sandwich configuration throughout the culture, whereas the cells on a single gel layer were eventually overgrown by non-hepatocyte cell types.

Functionally, hepatocytes cultured in the sandwich system also maintained better than those cultured on a single layer of collagen gel. Albumin production rates for these two systems were dramatically different. For the single gel system, albumin production was stable for the first three days but dropped precipitously to less than one-tenth that amount in one week. For the sandwich gel system, on the other hand, albumin production increased to three times the initial rate in a period of two weeks. Thereafter, albumin production rate gradually decreased, reaching roughly the initial rate by the seventh week. This difference is likely to be attributed to better maintenance of differentiation rather than to cell proliferation or cell death, as evidenced by the total DNA in each system, which followed a course of gradual decline similar to that of albumin production, reaching roughly 70% of the initial seeding DNA by the seventh week.

Albumin production was followed for cultures that were cultured on the first gel layer for varying periods of time before they were overlaid with the second layer. An increasing pattern of albumin production was observed for cultures that were overlaid with collagen for up to seven days after initial seeding.

To achieve a higher cell density culture initially, it was inadequate to simply double the number of cells seeded. For example, doubling the seeding cell density to 200,000 cells/cm$^2$ but keeping the depth of the medium constant at 2 mm resulted in mostly attached but non-viable cells; doubling the depth medium to 4 mm but keeping the cell density constant a 100,000/cm$^2$ gave similar result; halving the depth of medium to 1 mm and doubling the seeding cell density to 200,000 cells/cm$^2$, on the other hand, allowed twice the number of cells to attach and spread, achieving a confluent monolayer of cells after one day of culture.

EXAMPLE

Gel Suspension Configuration

Similar results can be obtained by providing extracellular matrix support for the hepatocytes in other configurations than the sandwich described above. For example, a gel suspension configuration can yield results comparable to those for the sandwich configuration. The gel suspension configuration is formed generally as follows. Collagen prepared as described above is added to a suspension of hepatocytes prepared above in (DMEM) media at 4° C. After 5 minutes, the collagen gel and cell suspension is warmed to 37° C., causing the collagen to gel. DMEM is then replaced with a small quantity of "complete" media and this media is subsequently changed daily.

EXAMPLE

Human Hepatocyte Culture

Human hepatocytes can be maintained in culture according to the invention in a manner similar to that described above.

Isolation of Human Hepatocytes.

Human hepatocytes for culture were successfully obtained from portions of resected livers in patients who are otherwise undergoing hepatic resections for metastatic or biliary diseases. These liver pieces were perfused with calcium-free (EDTA-containing) media for 10 minutes followed bo 0.5% collagenase for 20 minutes at 37° C. Vessels on the cut surfaces of the liver resections were cannulated with catheters and secured into position with 6-0 nylon purse-string sutures. At least 3 vessels and up to 8 vessels were cannuated in each resection; weights of perfused livers ranged 3–50 g. Viability of these isolations was generally >70% as estimated by trypan blue exclusion and cellular yields were approximately 1–10×10$^6$ cells per gram of liver.

Response of the morphology and protein secretory function of human hepatocytes in the sandwich configuration can be similar to that of the rat hepatocytes described above. Use Hepatocytes maintained according to the invention can be used to replace or augment liver function, by constructing a bioreactor having metabolic functions of the liver in vivo, and then either implanting the bioreactor into a recipient animal such as a patient having impaired liver function, or maintaining the bioreactor outside the body as an extracorporeal perfuspn system.

The hepatocytes supported in a configuration according to the invention can be arranged and configured so that an exchange or a flow of medium, such as, for example a perfusate such as blood or blood plasma; or a culture medium from which a product of hepatocyte metabolism, such as for example clotting factors, can be recovered; or a fluid from which a substance can be removed by the metabolic activity of the hepatocytes.

Other Embodiments

Other embodiments are within the following claims. For example, Other extracellular matrix components can be used to form the support, such as, for example, agarose, alginate, Type IV collagen, fibronectin, laminin, hyaluronic acid, and heparan sulfate, either alone or in combination.

Other cell types normally found in the liver, such as, for example, endothelial cells and Kupffer cells, can provide improved maintenance of the hepatocytes when cocultured with the hepatocytes in an extracellular support matrix configured according to the invention.

Other configurations than sandwiched collagen layers (flat-sheet) can be used for the support, such as, for example, collagen microcarriers coated with a second layer of collagen (spherical surfaces), immobilization of the cells within collagen beads (spherical), and immobilization of the cells outside hollow fibers (cylindrical). Such alternative configurations can serve to optimize such physicochemical characteristics of the hepatocyte maintenance system as transport properties for diffusion of oxygen, nutrients, and protein-bound toxins; mechanical and chemical stability properties of the matrices; and intrinsic hepatocyte reaction rates.

For implantation of the supported hepatocytes into a recipient's body, as for example to provide an intracorporeal artificial liver, membranes such as sodium alginate which do not generate an inflammatory reaction in the peritoneal cavity can be used to coat the hepatocyte transplatation systems for reducing immune cell rejection.

The hepatocytes can be seeded onto the first gel layer of the support at other densities. Cells at lower densities generally show virtually complete attachment and assume the normal morphology described above. If the seeding density is too great, however, most attached cells can be round and irregular, and these cells can also be functionally impaired, as evidenced by a lower albumin secretion rate. Also at the higher seeding densities, the cells tend to become clustered upon already attached cells, even when some unoccupied area remains on the surface of the first layer. Hepatocytes appear to be very metabolically active in culture, and can be very sensitive, for example, to availability of oxygen during the attachment process.

We claim:

1. A composition comprising a cultured hepatocyte in contact with a support comprising two layers, said support comprising sterilized collagen, said support having a configuration that permits said hepatocyte to form at least one apical surface and at least two discrete basal surfaces, wherein fewer than 1% of the cells present in the composition are non-hepatocytic cells.

2. A composition comprising a plurality of cultured hepatocytes sandwiched between two sterile supports, at least one of said supports comprising sterilized collagen, wherein at least a portion of said hepatocytes forms at least one apical surface and at least two discrete basal surfaces, and wherein fewer than 1% of the cells present in the composition are non-hedatocytic cells.

3. The composition of claim 1, wherein said matrix is agarose, alginate, fibronectin, laminin, hyaluronic acid, or heparan sulfate.

4. The composition of claim 2, wherein said matrix is agarose, alginate, fibronectin, laminin, hyaluronic acid, or heparan sulfate.

5. An artificial liver adapted for intracorporeal use comprising the composition of claim 1.

6. An artificial liver adapted for intracorporeal use comprising the composition of claim 2.

7. A bioreactor adapted for use in an extracorporeal perfusion system comprising the composition of claim 1.

8. A bioreactor adapted for use in an extracorporeal perfusion system comprising the composition of claim 2.

* * * * *

UNITED STATES PATENT AND TRADEMARK OFFICE
CERTIFICATE OF CORRECTION

PATENT NO. : 5,942,436
DATED : August 24, 1999
INVENTOR(S) : James Dunn et al

It is certified that error appears in the above-indentified patent and that said Letters Patent is hereby corrected as shown below:

ON TITLE PAGE

Item [73] Assignee :

Please add -- Massachusetts Institute of Technology, Cambridge, MA --.

Signed and Sealed this

Seventeenth Day of April, 2001

Attest:

NICHOLAS P. GODICI

Attesting Officer      Acting Director of the United States Patent and Trademark Office